US012226576B2

(12) United States Patent
Lu

(10) Patent No.: US 12,226,576 B2
(45) Date of Patent: Feb. 18, 2025

(54) MASK FOR PREVENTING WATER FROM ENTERING TRACHEAL STOMA

(71) Applicant: Li-An Lu, Taipei (TW)

(72) Inventor: Li-An Lu, Taipei (TW)

( * ) Notice: Subject to any disclaimer, the term of this patent is extended or adjusted under 35 U.S.C. 154(b) by 517 days.

(21) Appl. No.: 17/726,948

(22) Filed: Apr. 22, 2022

(65) Prior Publication Data

US 2023/0338685 A1 Oct. 26, 2023

(51) Int. Cl.
*A61M 16/04* (2006.01)
(52) U.S. Cl.
CPC ................................. *A61M 16/047* (2013.01)
(58) Field of Classification Search
CPC ....... A61M 16/0465–047; A61M 16/06–0655; A61M 2016/0661; A62B 18/00; A62B 18/02; A62B 23/00; A61C 5/90; A63B 71/085
See application file for complete search history.

(56) References Cited

U.S. PATENT DOCUMENTS

| | | | | |
|---|---|---|---|---|
| 4,274,406 A | * | 6/1981 | Bartholomew | A61M 16/06 128/912 |
| 5,485,837 A | * | 1/1996 | Solesbee | A61M 16/0465 128/207.14 |
| 5,947,121 A | * | 9/1999 | Marshall | A61M 16/047 128/207.15 |
| 6,668,831 B1 | * | 12/2003 | Hegwood | A61M 16/0465 128/207.14 |
| D536,442 S | * | 2/2007 | Berg | D24/110.4 |
| 2018/0147379 A1 | * | 5/2018 | Gammon | A61M 16/0488 |

FOREIGN PATENT DOCUMENTS

| CN | 111939414 A | 11/2020 |
|---|---|---|
| JP | 2020124467 A | 8/2020 |

* cited by examiner

*Primary Examiner* — Rachel T Sippel
(74) *Attorney, Agent, or Firm* — MUNCY, GEISSLER, OLDS & LOWE, P.C.

(57) ABSTRACT

A mask for preventing water from entering a tracheal stoma comprises a neck hanging part and a mask body connected with the neck hanging part. The mask body is worn on a tracheostomy patient through the neck hanging part. A concave space is formed on an inner side of the mask body, a plurality of air vents communicating with the concave space are formed in a lower half of an outer side of the mask body, and a plurality of inclined retaining walls are respectively located in the concave space and respectively connected to a top edge of each of the air vents, and the inclined retaining wall is capable of preventing the concave space from being seen when viewed directly through the air vents of the mask body. The mask of the invention is capable of greatly reducing a risk of water entering the tracheal stoma.

10 Claims, 10 Drawing Sheets

MASK FOR PREVENTING WATER FROM ENTERING TRACHEAL STOMA

FIELD OF THE INVENTION

The invention relates to a mask for a tracheal stoma, and more particularly to a mask for preventing water from entering a tracheal stoma.

BACKGROUND OF THE INVENTION

Tracheostoma is mainly used for breathing by tracheostomy patients. The tracheal stoma is directly connected to the trachea, any foreign objects entering the tracheal stoma will cause varying degrees of discomfort to the tracheostomy patient, in severe cases, the lungs will be damaged and the patient may die.

However, besides wiping, when tracheostomy patients need to clean the neck or head by taking a shower, they can only temporarily block the tracheal stoma in a very rough way with a large amount of gauze or other objects that do not affect breathing Although some manufacturers have produced masks that claim to be able to effectively prevent water ingress, the above-mentioned masks can only block water coming from in front of or above the head of the tracheostomy patient. However, it is known that when using a shower head to take a shower, it is very easy for water to splash and sprinkle, carelessness may cause the water sprayed toward the face from below. For this drawback, the existing masks are not designed to prevent water from entering, resulting in the water entering through the multiple air vents in a lower part of the mask and the water splashing inside the mask, causing a risk of the water entering the tracheal stoma accidentally.

Furthermore, JP Patent No. 2020124467A and CN Patent No. 111939414A respectively disclose the masks for tracheal stoma. In JP Patent No. 2020124467A, water infiltration is prevented by extending the water-vapor path through the partitions, but extending the water-vapor path increases the overall length of the tube to protrude prominently from the neck of the tracheostomy patient after wearing the mask. For the behavior of frequently switching actions in shower, the tracheostomy patient can easily come in contact accidentally with the tube protruding outward to a large extent, which will cause discomfort to the tracheostomy patient, and it is even easy for water to enter the tracheal stoma. Although CN Patent No. 111939414A discloses the technical content of using the protective cover to cover the tracheal stoma of the tracheostomy patient, the protective cover needs to be used with the breathing tube for the tracheostomy patient to breath through it, which is not conducive to showering conveniently.

SUMMARY OF THE INVENTION

A main object of the invention is to solve the problem that the conventional masks still have a high probability of causing water entering into a tracheal stoma.

In order to achieve the above object, the invention provides a mask for preventing water from entering a tracheal stoma comprising a neck hanging part and a mask body connected with the neck hanging part. A concave space is formed on an inner side of the mask body, a plurality of air vents communicating with the concave space are formed in a lower half of an outer side of the mask body, and a plurality of inclined retaining walls are located in the concave space and respectively connected to a top edge of each of the plurality of air vents, and the plurality of inclined retaining walls is capable of preventing the concave space from being seen when viewed directly through the air vents of the mask body.

In one embodiment, the outer side of the mask body includes an arcuate surface, and the plurality of air vents cannot be seen when viewing the arcuate surface from a top edge toward a bottom edge of the mask body.

In one embodiment, a recessed area is formed in the lower half of the outer side of the mask body, and the plurality of air vents is disposed on an edge of the recessed area.

In one embodiment, the recessed area is tapered from the bottom edge toward the top edge of the mask body.

In one embodiment, one end of each of plurality of inclined drainage walls not connected to one of the plurality of air vents is connected to one of the plurality of inclined retaining walls.

In one embodiment, the mask body includes a skirt disposed along an edge of the mask body.

In one embodiment, when viewed from a side of the mask body, the skirt includes a first inclined section and a second inclined section connected to the first inclined section and having a slope different from that of the first inclined section.

In one embodiment, the mask body includes a plurality of hanging ears formed on the skirt to assemble with the neck hanging part.

In one embodiment, the mask body includes at least one airtight ring disposed along the concave space.

Through the above-mentioned implementation of the invention, compared with the prior art, the invention has the following features: the plurality of inclined retaining walls of the invention are capable of preventing the concave space from being seen when viewed directly through the plurality of air vents of the mask body, and capable of blocking water from directly entering the concave space, ensuring that the tracheal stoma located in the concave space can be prevented water from entering. In addition, the plurality of inclined retaining walls are capable of causing water splashed thereon to be discharged toward the plurality of air vents, thereby enhancing an effect of preventing water from entering the tracheal stoma.

DETAILED DESCRIPTION OF THE PREFERRED EMBODIMENTS

The detailed description and technical content of the invention are described below with reference to the accompanying drawings.

Figure 1:
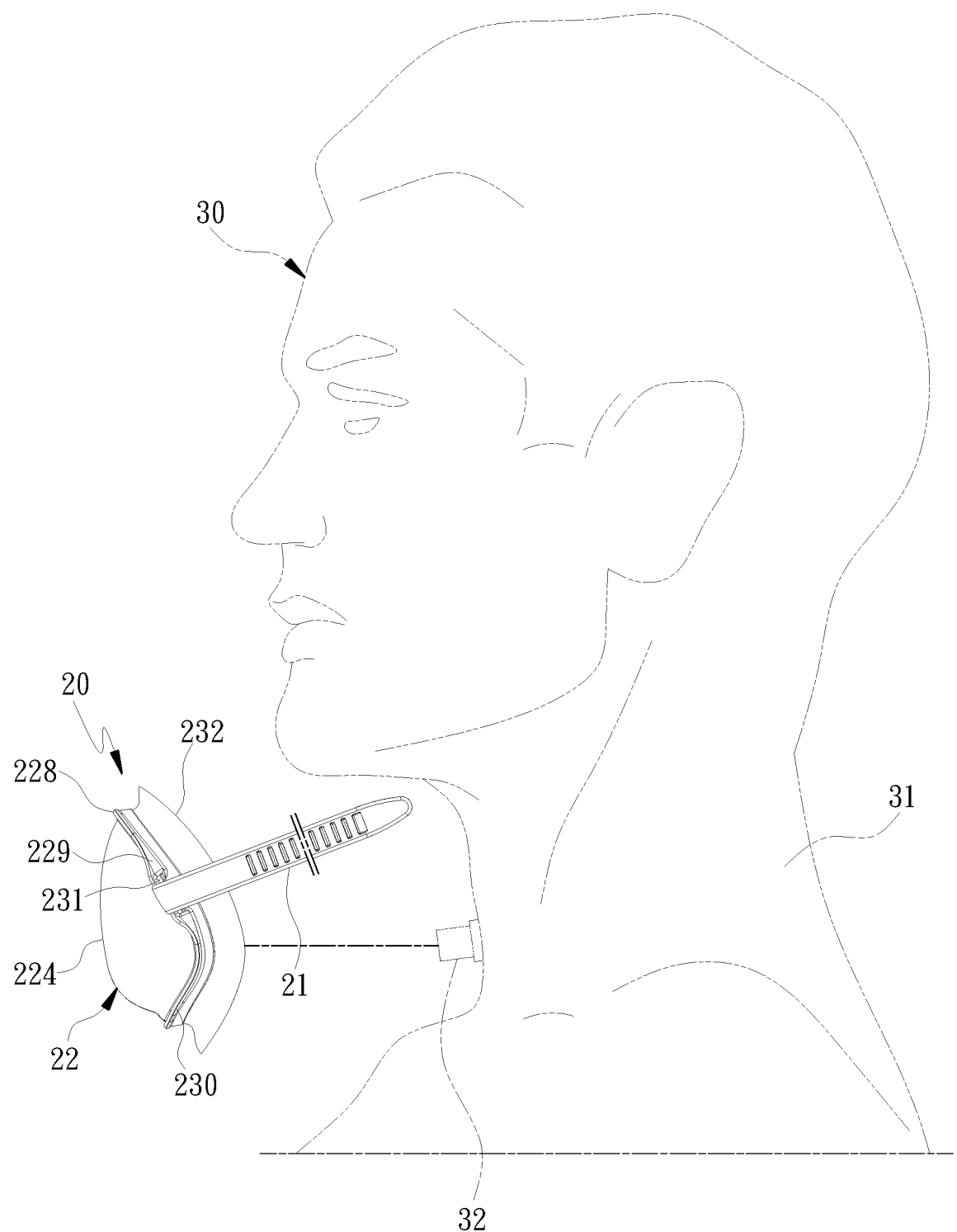
FIG. 1 is a schematic diagram of implementation of one embodiment of a mask of the invention.
Figure 2:
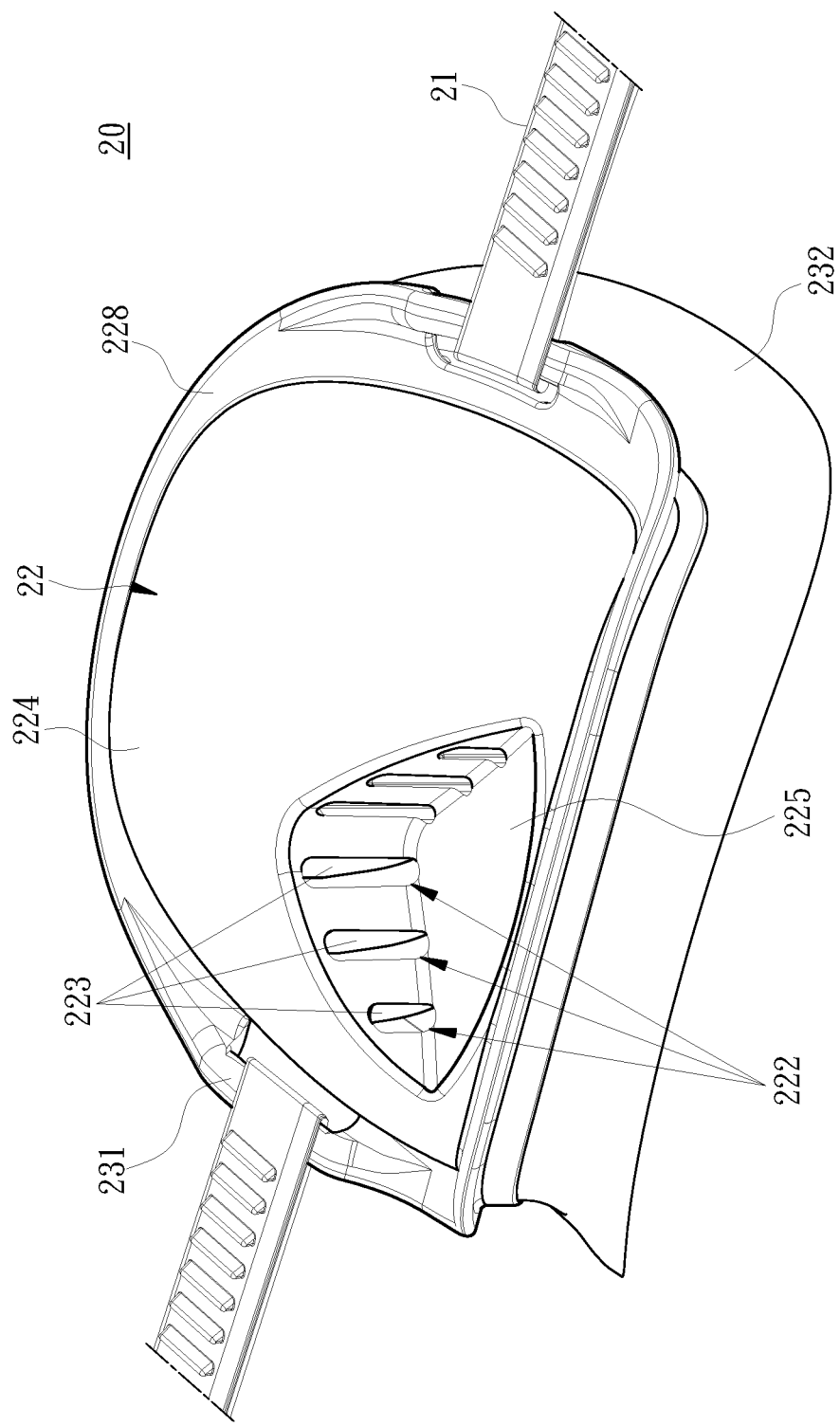
FIG. 2 is a perspective structural view of one embodiment of the mask of the invention.

Please refer to FIG. 1, the invention provides a mask 20, the mask 20 is mainly used to prevent water from entering a tracheal stoma 32 opened from a neck 31 of a tracheostomy patient 30 when the tracheostomy patient 30 takes a shower.

Please refer to FIG. 1, FIG. 2, FIG. 3, FIG. 4, FIG. 5, FIG. 6, FIG. 7 and FIG. 8, the mask 20 comprises a neck hanging part 21 and a mask body 22 connected to the neck hanging part 21. Wherein, the neck hanging part 21 is used as a main part for hanging the mask 20 on the tracheostomy patient 30, and the neck hanging part 21 can be an elastic band, a cord or other devices capable of achieving a same efficacy, the invention does not limit a way of implementing the neck hanging part 21.

Figure 9:
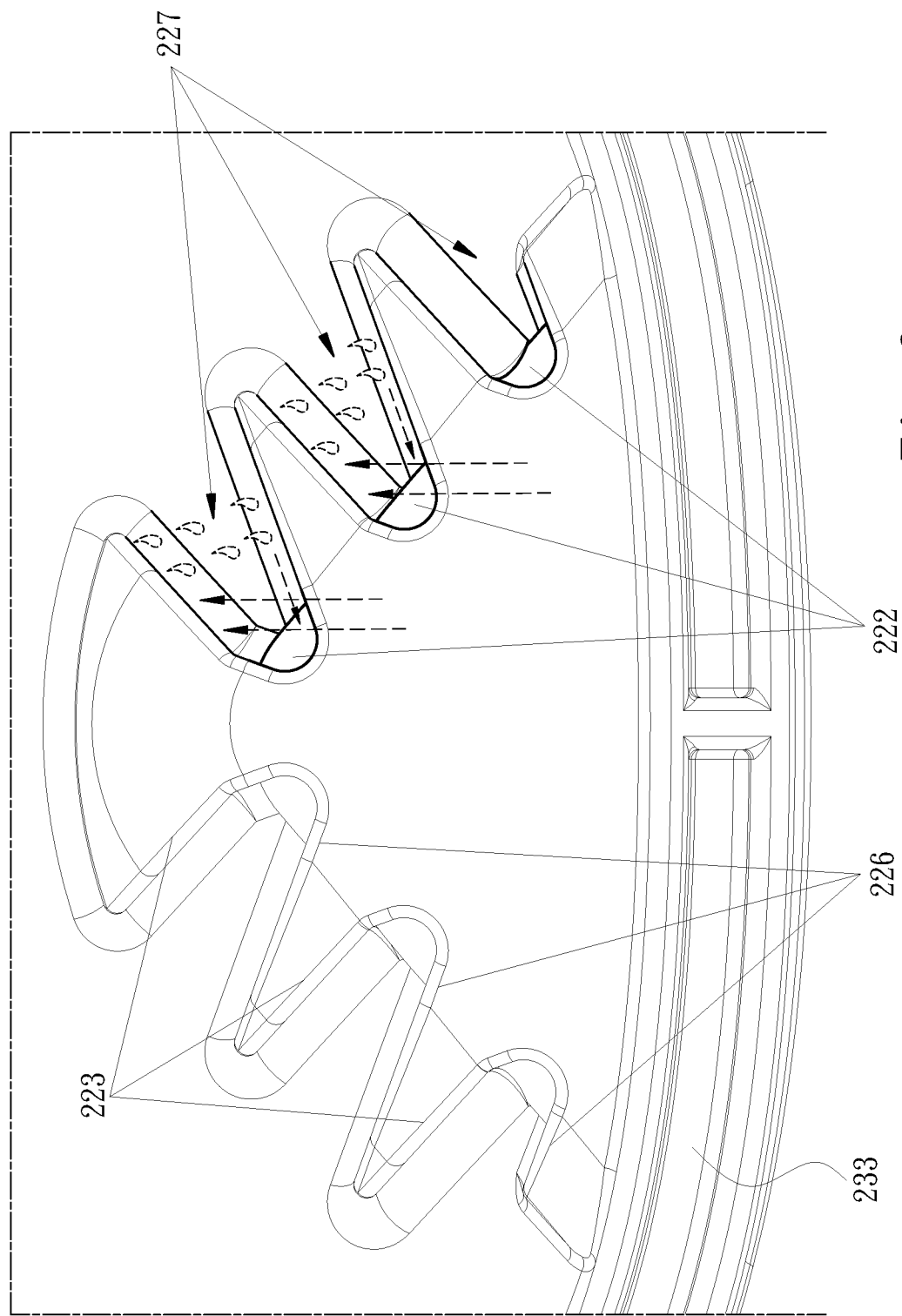
FIG. 9 is a schematic diagram of implementation of one embodiment of the mask body of the invention.

On the other hand, a concave space 221 is formed on an inner side of the mask body 22, a plurality of air vents 222 communicating with the concave space 221 are formed in a lower half of an outer side of the mask body 22, and a plurality of inclined retaining walls 223 are located in the concave space 221 and respectively connected to a top edge of each of the air vents 222. A range of the concave space 221 is at least big enough such that the tracheal stoma 32 can be properly positioned therein and a proper breathing space can be reserved. In addition, the plurality of air vents 222 serve as bridges for the concave space 221 to communicate with outside, and the plurality of air vents 222 are not limited to united shape and united size. Please refer to FIG. 5 and FIG. 6, each of the plurality of inclined retaining walls 223 is respectively connected to the top edge of one of the plurality of air vents 222, so that the concave space 221 can be prevented from being seen when viewed directly through the plurality of air vents 222 of the mask body 22. Thereby, the tracheostomy patient 30 uses a shower head to take a shower, when shower water sprayed toward the plurality of air vents 222 caused by careless manipulation, the shower water will not be able to enter the concave space 221 due to being blocked by the inclined retaining walls 223, such that the tracheal stoma 32 located in the concave space 221 can be prevented from ingress of water, as shown in FIG. 9. In addition, the shower water splashed on the plurality of inclined retaining walls 223 can be discharged toward the plurality of air vents 222, thereby enhancing an effect of preventing water from entering the tracheal stoma 32.

Figure 7:
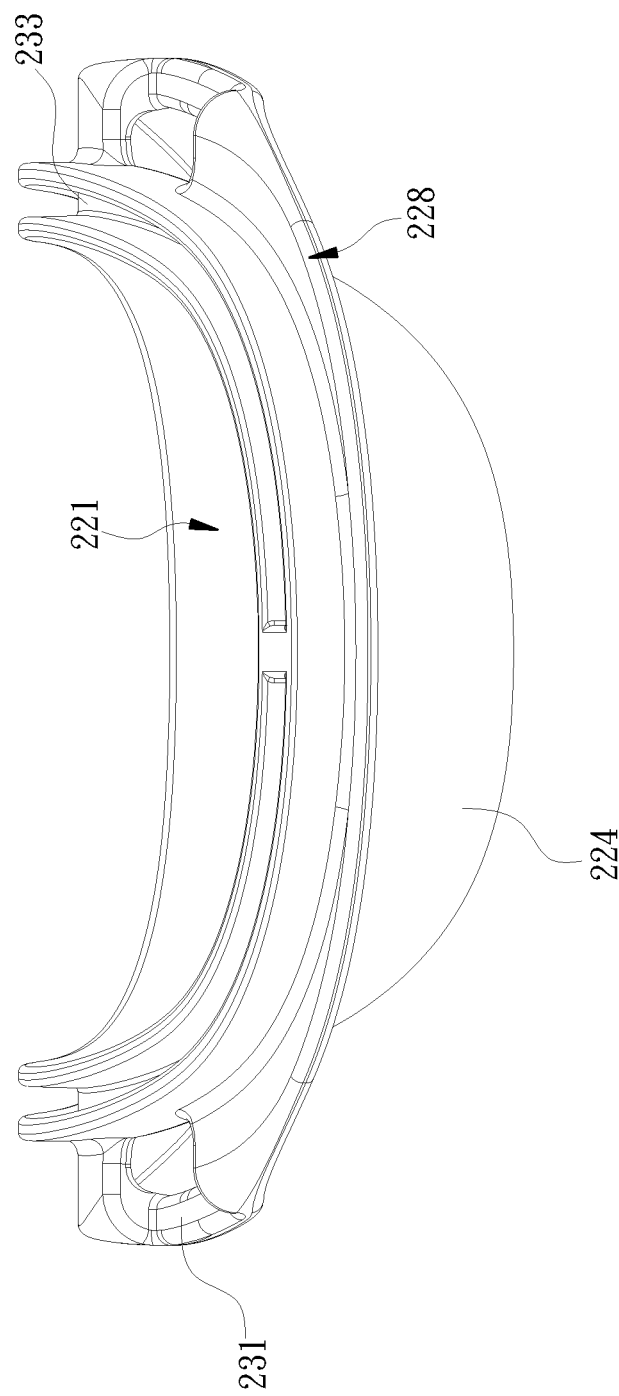
FIG. 7 is a top view of one embodiment of the mask body of the invention.

Please refer to FIG. 1 and FIG. 8, the inner and outer sides of the mask body 22 are defined hereinafter in this specification. The inner side refers to a side of the mask body 22 facing the tracheal stoma 32, and the outer side refers to a side of the mask body 22 that does not face the tracheal stoma 32, and the outer side is served as a side of an outer surface when the mask body 22 is worn. Accordingly, in one embodiment, the outer side of the mask body 22 includes an arcuate surface 224, and the plurality of air vents 222 cannot be seen when viewing the arcuate surface 224 from a top edge toward a bottom edge of the mask body 22, as shown in FIG. 7. Further, water splashed on the arcuate surface 224 flows toward the bottom edge of the mask body 22. Please refer to FIG. 4, FIG. 5 and FIG. 8, in one embodiment, a recessed area 225 is formed in the lower half of the outer side of the mask body 22, and the plurality of air vents 222 are disposed on an edge of the recessed area 225. Furthermore, the recessed area 225 is tapered from the bottom edge toward the top edge of the mask body 22. Further, the recessed area 225 is roughly triangular, and the plurality of air vents 222 is respectively located on two adjacent sides of the aforementioned triangle.

Figure 3:
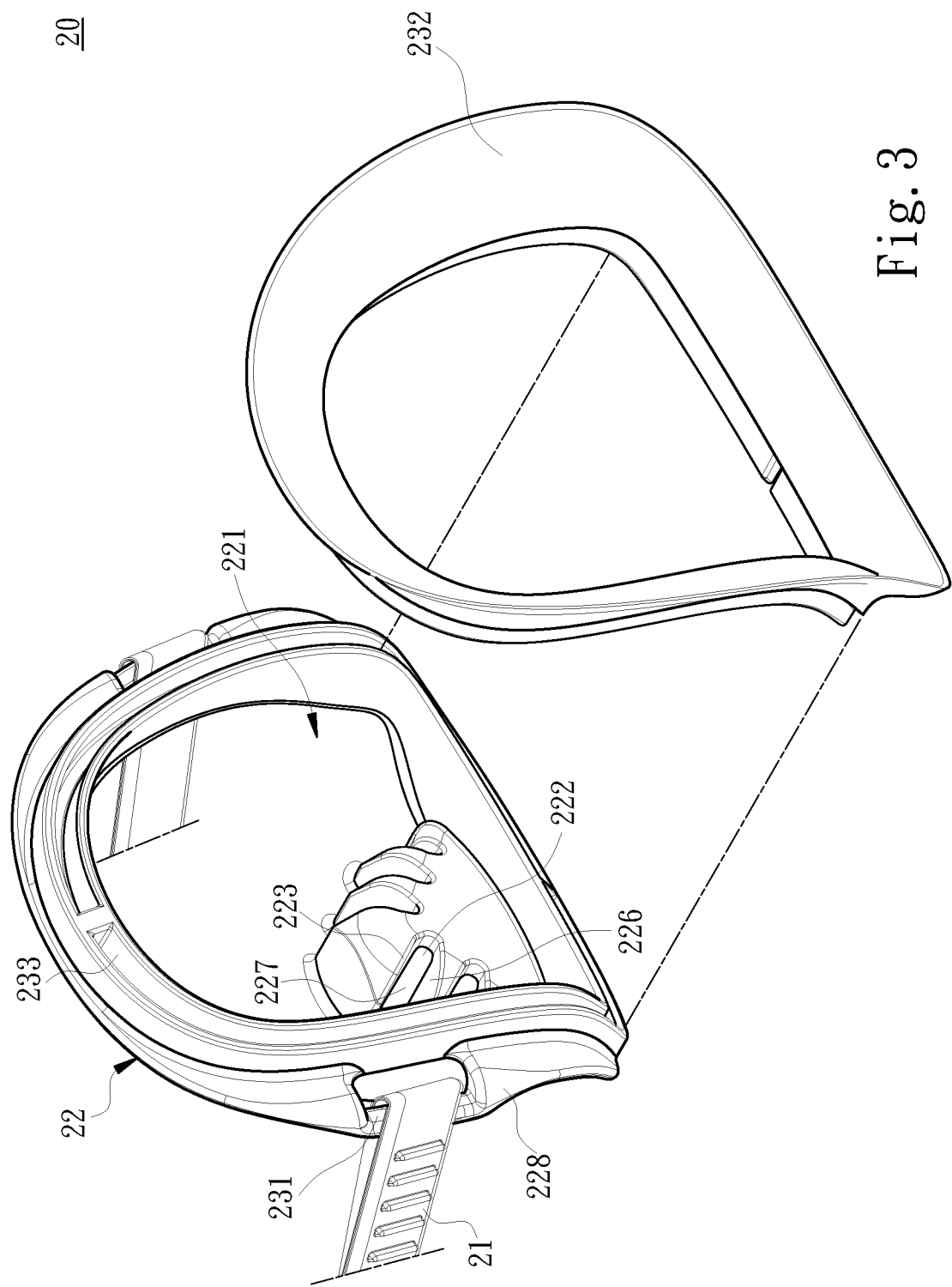
FIG. 3 is a perspective exploded view of partial structures of one embodiment of the mask of the invention.
Figure 4:
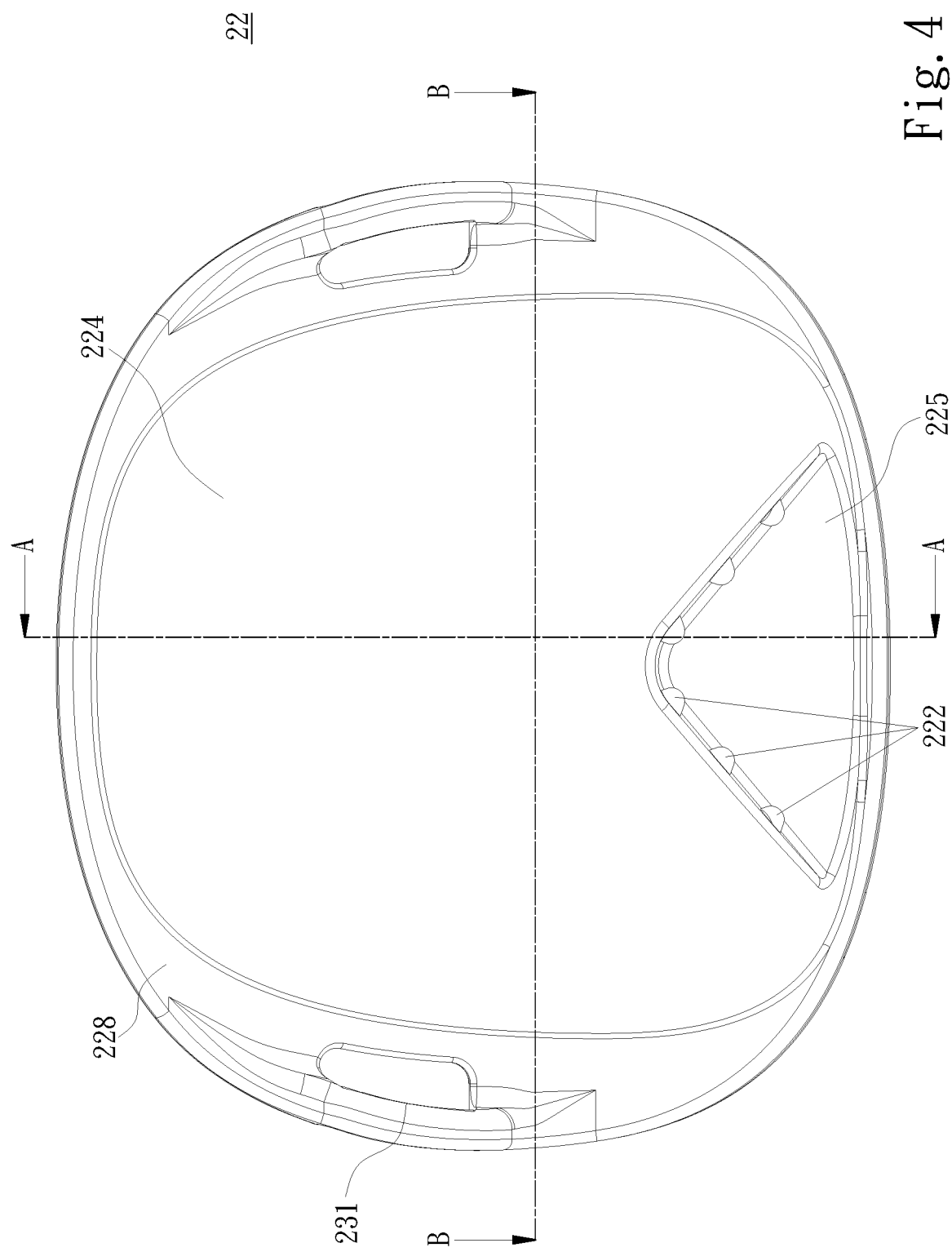
FIG. 4 is a front view of one embodiment of a mask body of the invention.
Figure 5:
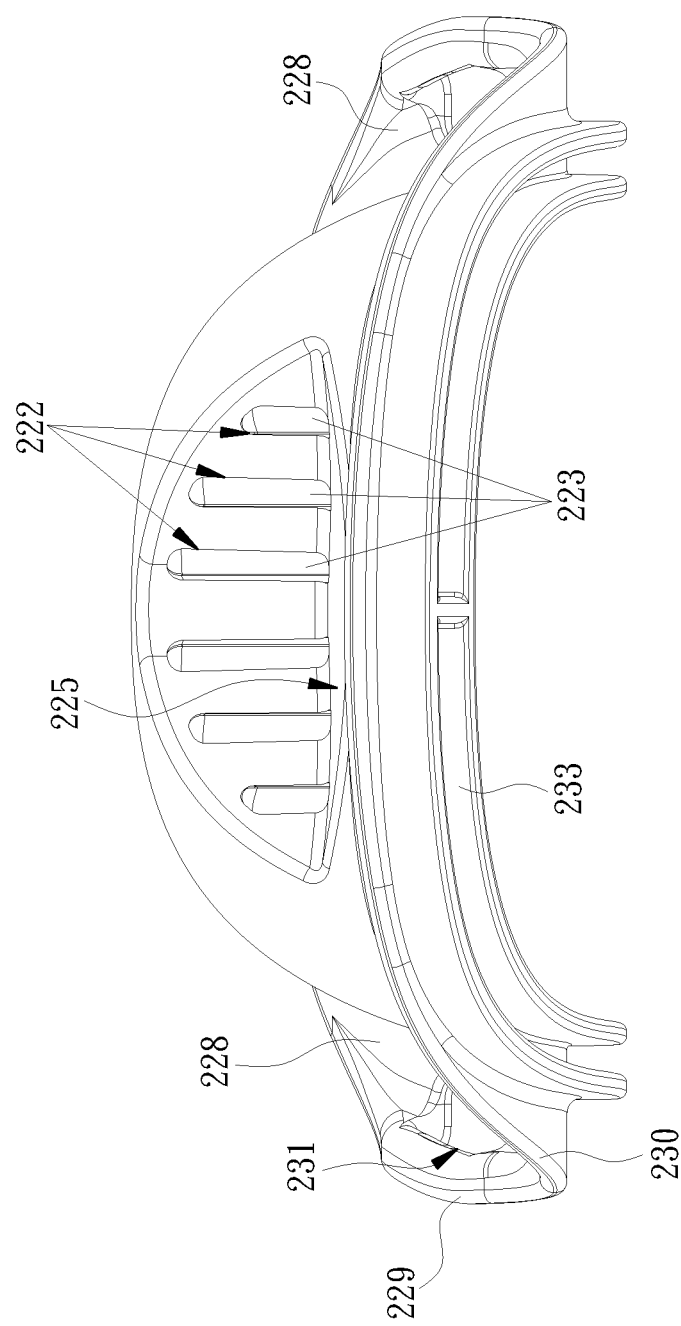
FIG. 5 is a bottom view of one embodiment of the mask body of the invention.
Figure 6:
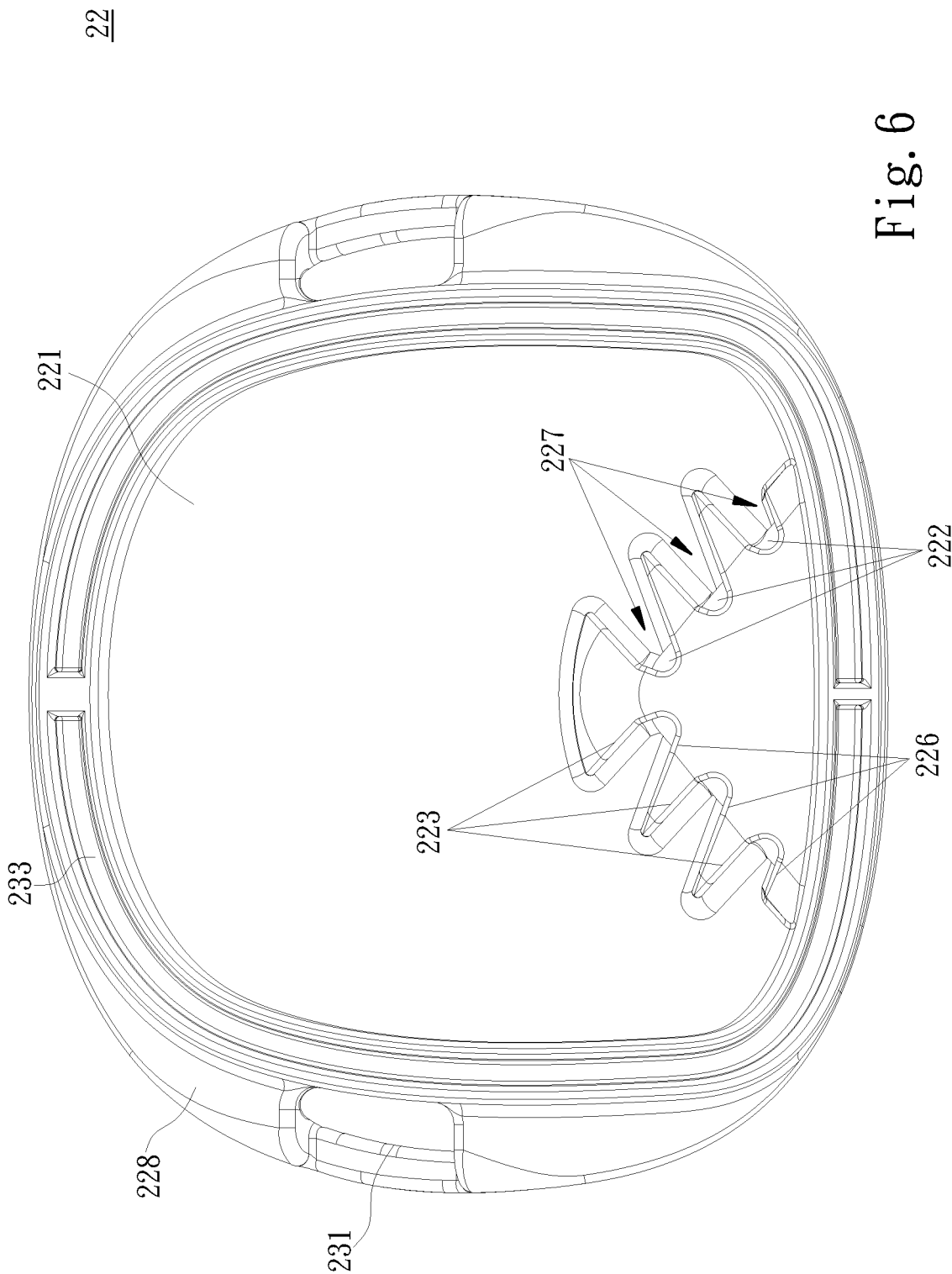
FIG. 6 is a rear view of one embodiment of the mask body of the invention.

Please refer to FIG. 3 and FIG. 6 again, in one embodiment, the mask body 22 includes a plurality of inclined drainage walls 226 located in the concave space 221 and respectively connected to each of the plurality of air vents 222. Further, each of the plurality of inclined drainage walls 226 is respectively opposite to each of the plurality of inclined retaining walls 223. Furthermore, each of the inclined drainage walls 226 and each of the inclined retaining walls 223 opposite to each other jointly define a channel 227, and the channel 227 is communicated and tapered toward one of the plurality of air vents 222 due to configuration of one of the plurality of inclined drainage walls 226 and one of the plurality of inclined retaining walls 223 that jointly define the channel 227; that is, the channel 227 is trumpet-shaped, that is, the channel 227 is gradually expanded from one of the plurality of air vents 222, thereby this design is capable of reducing a flow rate of an airflow entering from one of the plurality of air vents 222 due to the channel 227. If water accidentally enters the channel 227, this design is also capable of reducing a flow rate of the water, and due to an effect of gravity, the water will flow downward and back to one of the plurality of air vents 222, further reducing a possibility of the tracheostomy patient 30 inhaling water inadvertently. In one embodiment, one end of each of the plurality of inclined drainage walls 226 not connected to one of the plurality of air vents 222 is connected to one of the plurality of inclined retaining walls 223.

Please refer to FIG. 1, FIG. 2, FIG. 3, FIG. 4, FIG. 5, FIG. 6 and FIG. 7. In one embodiment, the mask body 22 includes a skirt 228 disposed along an edge of the mask body 22, the skirt 228 receives splashed water during showering and prevents water from approaching a position where the mask body 22 is in contact with a body of the tracheostomy patient 30. In another embodiment, when viewed from a side of the mask body 22, the skirt 228 includes a first inclined section 229 and a second inclined section 230 connected to the first inclined section 229. Wherein, a slope of the second inclined section 230 is different from that of the first inclined section 229. On the other hand, in one embodiment, the mask body 22 includes a plurality of hanging ears 231 formed on the skirt 228 to assemble with the neck hanging part 21.

Figure 8:
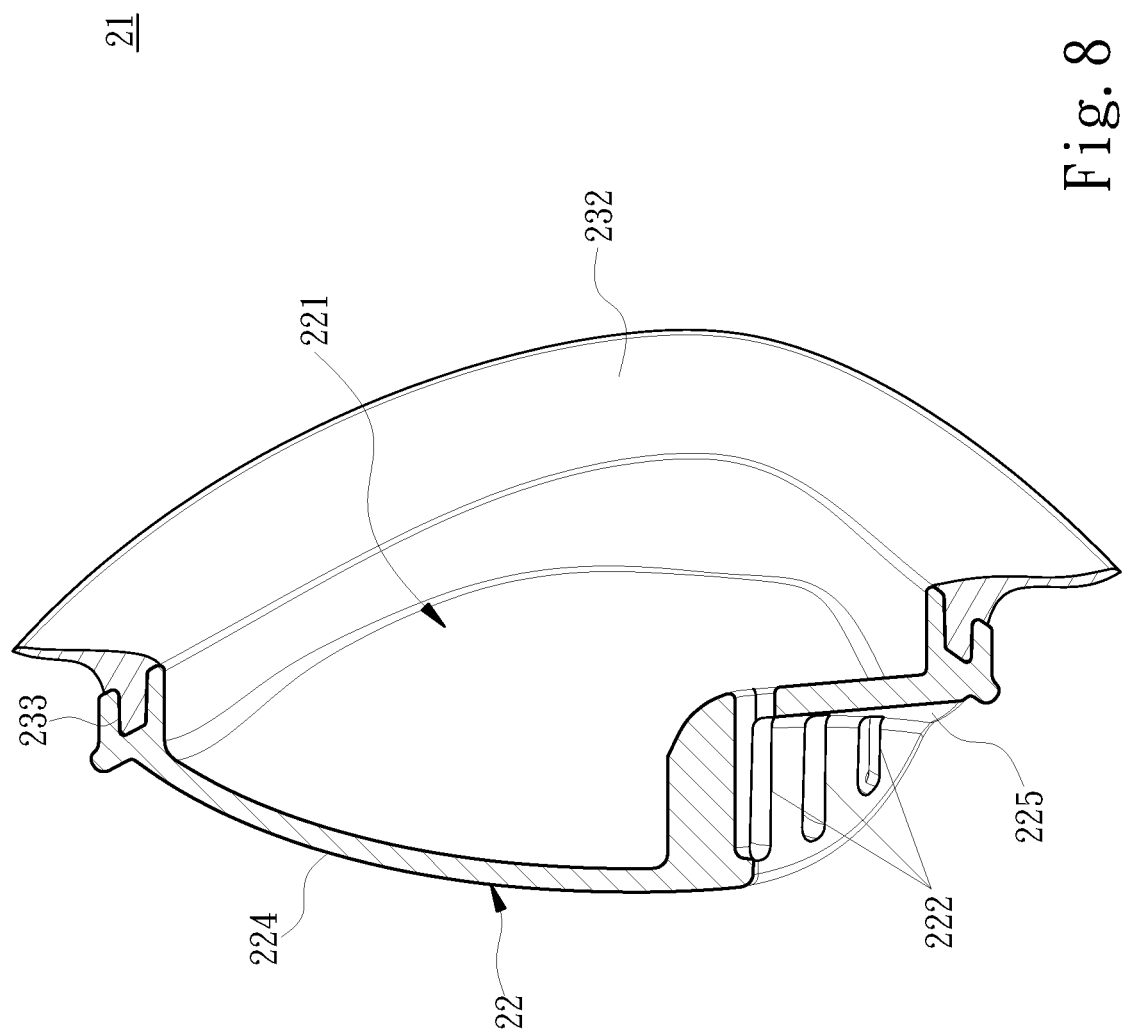
FIG. 8 is a cross-sectional view of section line A-A of the mask body in FIG. 4.

Please refer to FIG. 3 and FIG. 8. In one embodiment, the mask body 22 includes an airtight ring 232 disposed along the concave space 221. The airtight ring 232 can be formed integrally with the mask body 22 or implemented by assembling on the mask body 22 by another component. If the airtight ring 232 is another component, the mask body 22 needs to have an annular assembly portion 233 formed along the concave space 221, the annular assembly portion 233 needs to be designed to match the airtight ring 232, and can be a groove or a rib.

Figure 10:
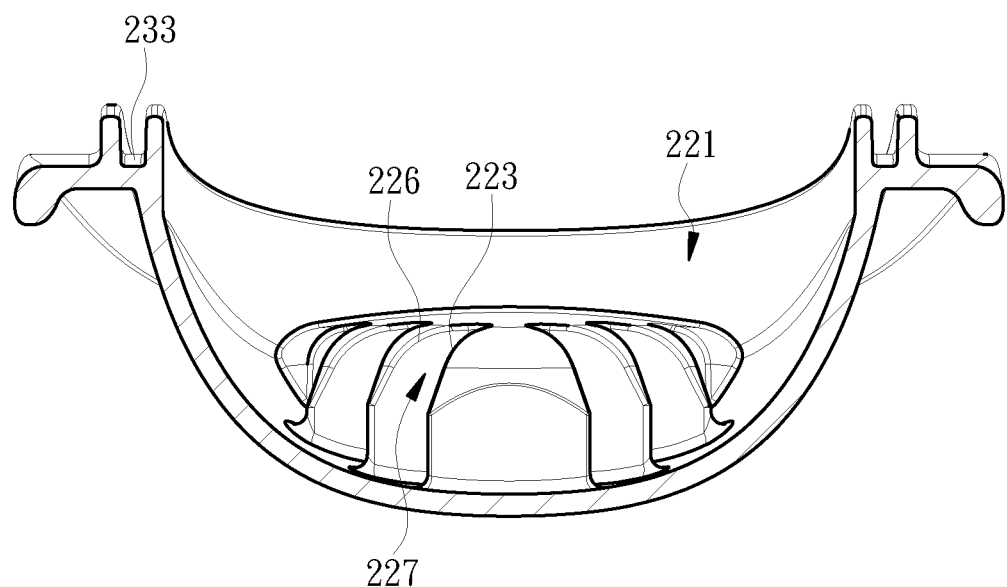
FIG. 10 is a cross-sectional view of section line B-B of the mask body in FIG. 4.
Figure 11:
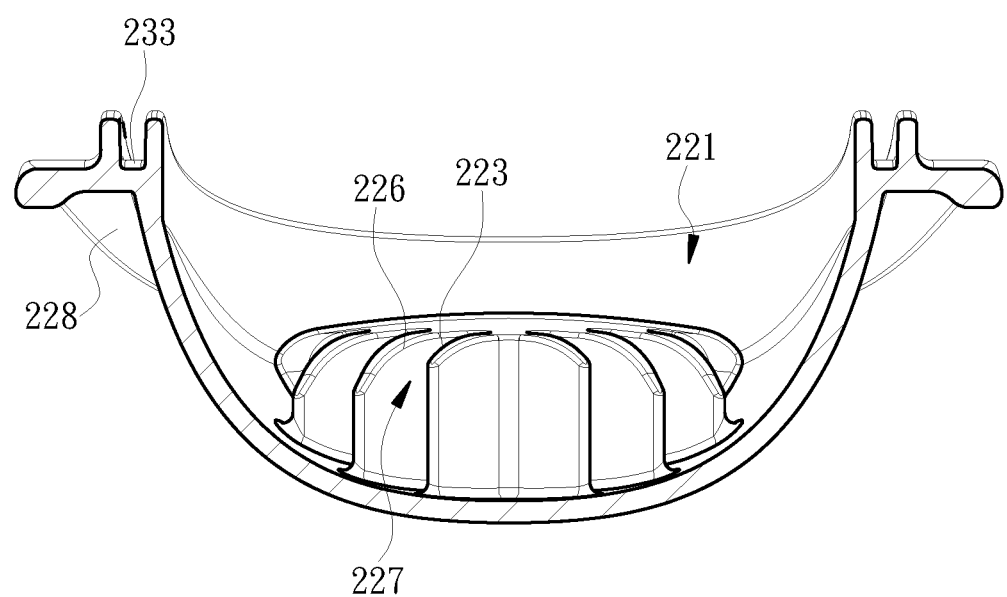
FIG. 11 is a cross-sectional view of another embodiment of the mask body of the invention.

Please refer to FIG. 10 and FIG. 11, a length of each of the plurality of inclined retaining walls 223 of the invention can be adjusted according to implementation requirements. For example, the mask body 22 can be provided with the plurality of inclined drainage walls 226 corresponding to the plurality of inclined retaining walls 223, or a length of each of the plurality of inclined drainage walls 226 can also be adjusted according to a design of the plurality of inclined retaining walls 223.

What is claimed is:

1. A mask for preventing water from entering a tracheal stoma comprising:
   a neck hanging part; and
   a mask body connected with the neck hanging part, a concave space being formed on an inner side of the mask body, a plurality of air vents communicating with the concave space being formed in a lower half of an outer side of the mask body, and a plurality of inclined retaining walls being located in the concave space and respectively connected to a top edge of each of the plurality of air vents, and the plurality of inclined retaining walls being capable of preventing the concave space from being seen when viewed directly through the plurality of air vents of the mask body.

2. The mask for preventing water from entering the tracheal stoma as claimed in claim 1, wherein the outer side of the mask body comprises an arcuate surface, and the plurality of air vents cannot be seen when viewing the arcuate surface from a top edge toward a bottom edge of the mask body.

3. The mask for preventing water from entering the tracheal stoma as claimed in claim 2, wherein a recessed area is formed in the lower half of the outer side of the mask body, and the plurality of air vents are disposed on an edge of the recessed area.

4. The mask for preventing water from entering the tracheal stoma as claimed in claim 3, wherein the recessed area is tapered from the bottom edge toward the top edge of the mask body.

5. The mask for preventing water from entering the tracheal stoma as claimed in claim 1, wherein the mask body comprises a plurality of inclined drainage walls located in the concave space and respectively connected to each of the plurality of air vents.

6. The mask for preventing water from entering the tracheal stoma as claimed in claim 5, wherein one end of each of the plurality of inclined drainage walls not connected to one of the plurality of air vents is connected to one of the plurality of inclined retaining walls.

7. The mask for preventing water from entering the tracheal stoma as claimed in claim 1, wherein the mask body comprises a skirt disposed along an edge of the mask body.

8. The mask for preventing water from entering the tracheal stoma as claimed in claim 7, wherein when viewed from a side of the mask body, the skirt comprises a first inclined section and a second inclined section connected to the first inclined section and having a slope different from that of the first inclined section.

9. The mask for preventing water from entering the tracheal stoma as claimed in claim 7, wherein the mask body comprises a plurality of hanging ears formed on the skirt to assemble with the neck hanging part.

10. The mask for preventing water from entering the tracheal stoma as claimed in claim 1, wherein the mask body comprises at least one airtight ring disposed along the concave space.

* * * * *